United States Patent [19]

Ogawa

[11] 4,279,486
[45] Jul. 21, 1981

[54] FILM TAKEUP DEVICE FOR AN ENDOSCOPE HAVING A CAMERA HOUSED IN A DISTAL END PORTION OF AN ENDOSCOPE SHEATH

[75] Inventor: Mototugu Ogawa, Chofu, Japan

[73] Assignee: Olympus Optical Co., Ltd., Tokyo, Japan

[21] Appl. No.: 88,752

[22] Filed: Oct. 29, 1979

Related U.S. Application Data

[63] Continuation of Ser. No. 882,064, Feb. 28, 1978, abandoned.

[30] Foreign Application Priority Data

Mar. 4, 1977 [JP] Japan .......................... 52-26191[U]

[51] Int. Cl.³ .................... G03B 29/00; A61B 1/06
[52] U.S. Cl. ................................ 354/62; 128/6;
354/63; 354/212; 74/501 R; 242/71
[58] Field of Search .......................... 128/4–8;
242/71.1, 71, 71.2, 71.6; 74/110, 501 R; 403/41,
109, 104, 395, 398; 354/62

[56] References Cited

U.S. PATENT DOCUMENTS

| | | | |
|---|---|---|---|
| 2,865,225 | 12/1958 | Huffman | 74/110 |
| 3,866,602 | 2/1975 | Furihata | 128/6 |
| 3,892,228 | 7/1975 | Mitsui | 128/4 |
| 4,038,977 | 8/1977 | Okada | 128/6 |

FOREIGN PATENT DOCUMENTS 45-25832  8/1970  Japan ................................ 128/6

*Primary Examiner*—Robert W. Michell
*Assistant Examiner*—Arthur S. Rose

[57] ABSTRACT

A film takeup device for an endoscope comprises a takeup mechanism provided in an endoscope operation section; an operating wire section for transmitting the action of the takeup mechanism to a rolled film received in a distal end portion of an endoscope sheath, thereby feeding the rolled film one frame after another; and a wire length-adjusting unit disposed in the operating wire section and wherein, when the rolled film is attached to and removed from the distal end portion of the endoscope sheath, a connector for connecting the rolled film with the operating wire section is drawn out of the distal end portion of the endoscope sheath due to the wire length-adjusting unit being extended long, thereby enabling the rolled film to be easily and reliably connected to the operating wire section and removed therefrom.

5 Claims, 12 Drawing Figures

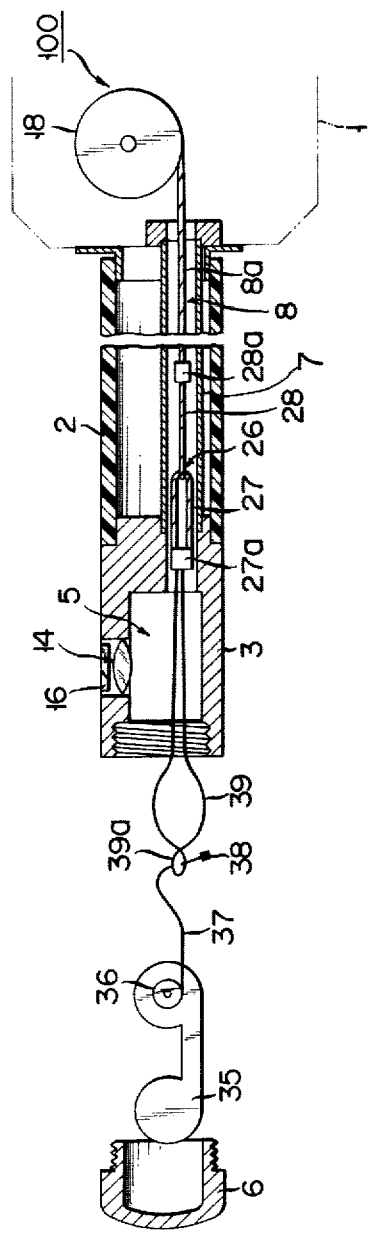
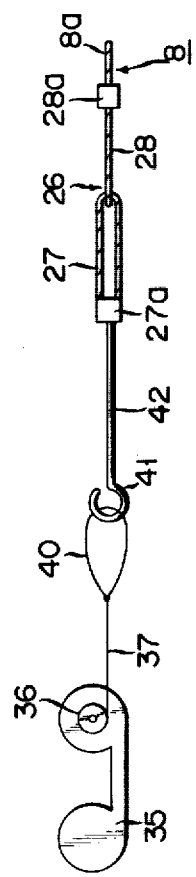
FIG. 11
FIG. 12

FILM TAKEUP DEVICE FOR AN ENDOSCOPE HAVING A CAMERA HOUSED IN A DISTAL END PORTION OF AN ENDOSCOPE SHEATH

This is a continuation of application Ser. No. 882064, filed Feb. 28, 1978, now abandoned.

BACKGROUND OF THE INVENTION

This invention relates to improvements on a film takeup device for an endoscope having a camera received in a distal end portion of an endoscope sheath.

Recently, an endoscope has been developed which has a camera received in a distal end portion of an endoscope sheath and a film loaded in the distal end portion, thereby photographing the interior of a coelom or body cavity of human or other living beings. A film takeup device for this type of endoscope generally comprises a takeup mechanism including a pulley provided in an operation section of the endoscope, and an operating wire connected to a leading end of a film loaded in a distal end portion of an endoscope sheath or wound about a pulley provided on a takeup shaft of a film cassette. With the above-mentioned arrangement, a rolled film is fed one frame after another, each time the takeup mechanism is operated. Before a rolled film or a film cassette is loaded in the distal end portion of the endoscope sheath, the operating wire is unwound from the takeup mechanism, causing the leading end of the operating wire to be pushed into a film chamber or film cassette chamber, and then the leading end of the film or a film takeup wire wound about the pulley provided on the takeup shaft of the film cassette is connected to the engagement portion of the leading end of the operating wire. Therefore, the longer the leading end portion of the operating wire extended into the above-mentioned chamber, the easier the connection between the operating wire and the film or the film takeup wire.

Where, however, the leading end of the operating wire is extended too much into the aforesaid chamber, the tip of the leading end portion of the operating wire strikes against the inner wall of a cap which closes the tip of the distal end portion of the endoscope sheath, with the possibility of the leading end portion of the operating wire being bent or broken. For this reason, the extent to which the leading end portion of the operating wire is carried into the aforesaid chamber is so restricted that the tip of the leading end portion is prevented from contacting the inner wall of the cap. Therefore, connection between the operating wire and the film or the film takeup wire has presented considerable difficulties, consuming a great deal of time. Moreover, since this connecting work is generally undertaken in a semi-dark chamber, it is not easy to judge whether the connection has been effected reliably, unavoidably leading to an error in the connection.

For resolution of the above-mentioned problems, it may be contemplated to elongate the cap. However, this arrangement is not available for practical application because of the drawbacks that the rigid distal end portion of the endoscope sheath has to be extended, not only presenting difficulties in inserting the distal end portion into the body cavity of human beings, but also causing a patient to feel great pain at the time of the insertion.

SUMMARY OF THE INVENTION

An object of this invention is to provide a film takeup device for an endoscope, wherein an operating wire section is provided with means for adjusting its length; when the operating wire section is unwound, the leading end portion of the operating wire section is pushed for a short distance into the chamber of the distal end portion of the endoscope sheath; and yet the leading end portion of the operating wire section can be manually drawn long out of the tip of the distal end portion of the endoscope sheath, thereby enabling the film to be easily attached to the operating wire section and detached therefrom.

Another object of the invention is to provide a film takeup device for an endoscope which easily attains the attachment and detachment without the necessity of rendering the rigid distal end portion of the endoscope sheath longer than is customarily required.

According to this invention, there is provided an endoscope including an operation section, a sheath connected to the operation section and designed to receive a camera and rolled film in its distal end portion, and a film takeup device, wherein the film takeup device comprises a takeup mechanism disposed in the operation section; an operating wire section extending into the sheath to feed the film one frame after another, each time the takeup mechanism is actuated; and wire length-adjusting means provided in the operating wire section and, when pulled out of the distal end of the sheath, designed to extend the operating wire section.

The wire length-adjusting means may be formed of two or three linked loops of metal wires. This construction causes the loops to overlap each other when the operating wire section is carried toward the distal end portion of the sheath when the operating wire is unwound by the takeup mechanism. As a result, the operating wire section has its length shortened. However, as the operating wire section is pulled out of the distal end portion of the sheath, the loops overlap lesser and lesser to allow the leading end of the operating wire section to be easily drawn out of the distal end portion of the sheath. As a result, the film can be easily and reliably attached to the operating wire section and removed therefrom, and moreover the leading end of the operating wire section is prevented from being bent or broken.

BRIEF DESCRIPTION OF THE DRAWING

FIGS. 11 and 12 are longitudinal sectional views of the gastrocamera of FIG. 3, where the film cartridge is replaced by a film cassette.

DESCRIPTION OF THE PREFERRED EMBODIMENTS

There will now be described a film takeup device embodying this invention which is applied to a gastrocamera, a kind of endoscope. Obviously, the invention can be adapted for use with any other type of endoscope. Throughout the drawings, the same or similar parts are denoted by the same numerals.

Figure 1:
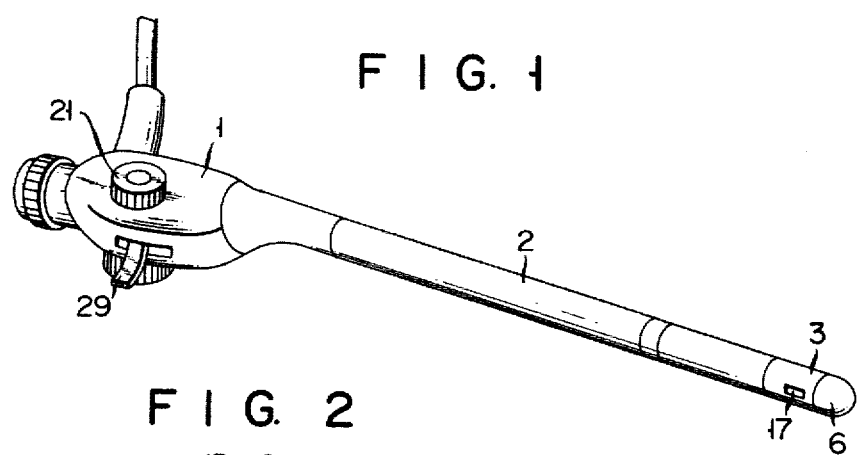
FIG. 1 is a perspective view of a gastrocamera, a kind of endoscope, to which a film takeup device embodying this invention is applied.

Referring to FIG. 1, the gastrocamera comprises an operation section 1; a flexible sheath 2 whose proximal end is connected to the operation section 1; and a rigid distal end portion 3 formed at the distal end of the sheath 2.

Figure 2:
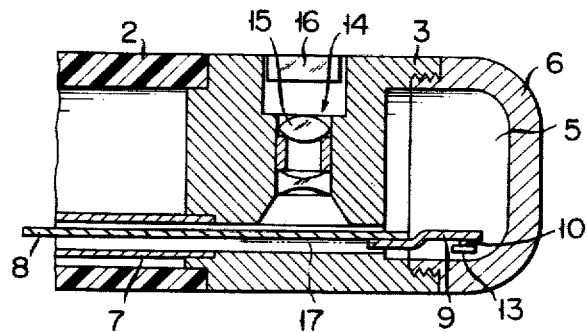
FIG. 2 is a longitudinal sectional view of the distal end portion of the sheath of FIG. 1.

Referring to FIG. 2, a film chamber 5 for receiving a film container such as a film cartridge 4 (FIG. 3) is formed in the distal end portion 3 of the sheath 2. The outer end of the film chamber 5 is normally covered with a round headed cap 6 by threaded engagement.

Figure 4:
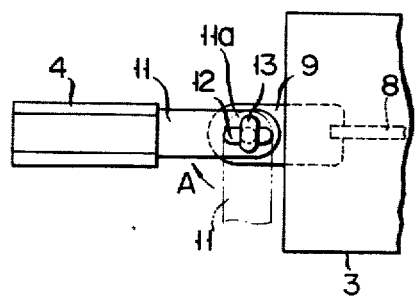
FIG. 4 is a plan view showing a connection between the leading end of a rolled film and the corresponding end of an operating wire in the gastrocamera in FIGS. 2 and 3.
Figure 3:
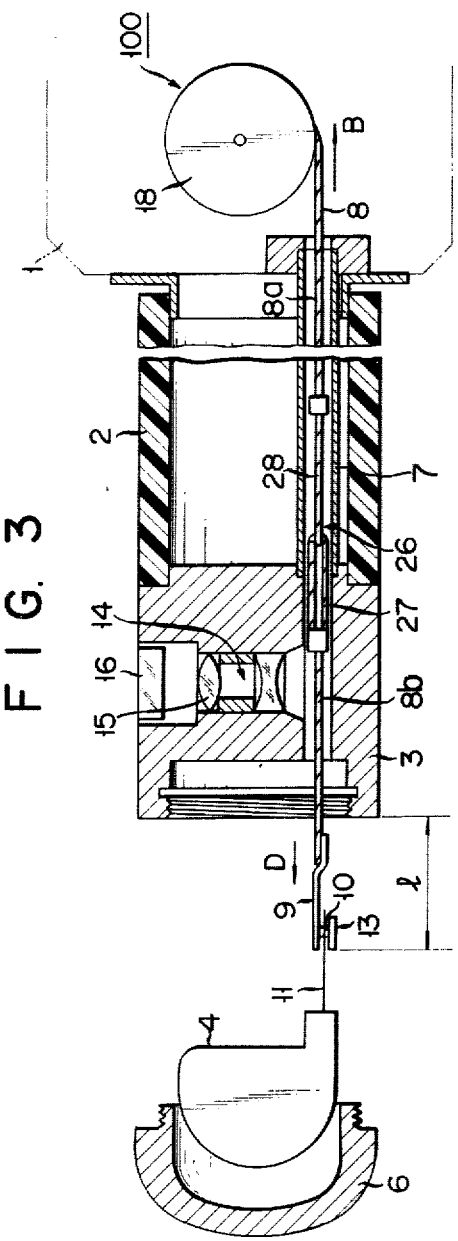
FIG. 3 is a longitudinal sectional view of the distal end portion of the sheath of FIG. 1, where the cap is taken off the tip of the distal end portion of the sheath and a film cartridge is removed from the film chamber.

Referring to FIGS. 3 and 4, a flexible guide tube 7 lengthwise extends through the sheath 2. An operating wire section 8 extends from the operation section 1 through the guide tube 7 into the distal end portion 3 of the sheath 2. The tip of the operating wire section 8 is fitted with a plate-like film connector 9 including a T-shaped engaging pin 10. A rod-like stop element 13 is integrally formed on the upper end of the T-shaped engaging pin 10. This stop element 13 extends parallel with the facing surface of the film connector 9 and crosswise thereof. A leading end portion 11a of a film 11 being drawn out of the film cartridge 4 is bored with an elongate hole 12 extending lengthwise of the film 11. As shown in dotted lines in FIG. 4, the leading end portion 11a sets the film 11 substantially at right angles to the film connector 9. After the stop element 13 is let to pass through the elongate hole 12, the film 11 is rotated through an angle of approximately 90° in the direction of an arrow A to take a solid line position. This operation causes the stem of the T-shaped engaging pin 10 to be inserted into the elongate hole 12 bored in the leading end portion 11a of the film 11. Since the stop element 13 is longer than the width of the elongate hole 12, the leading end portion 11a of the film 11 is prevented from coming off the T-shaped engaging pin 10. Thus, the leading end portion 11a of the film 11 is firmly connected to the film connector 9. After this connection, the film cartridge 4 is placed in the film chamber 5. When a later described takeup mechanism 100 is operated, the operating wire section 8 is pulled in the direction of an arrow B shown in FIG. 3 to a prescribed extent each time, causing the film 11 to be pulled out of the film cartridge 4 by one frame.

Referring to FIGS. 2 and 3, a camera generally denoted by referential numeral 14 is received in the distal end portion 3 of the sheath 2. A lens system 15 of the camera 14 focuses light beams entering through a photographing window 16 (FIG. 2) bored in the lateral wall of the distal end portion 3 of the sheath 2 onto a focusing plane 17 (FIG. 2) in which the sensitized surface of the film 11 is positioned, thereby photographing the inner wall of the gastrocoel.

Figure 5:
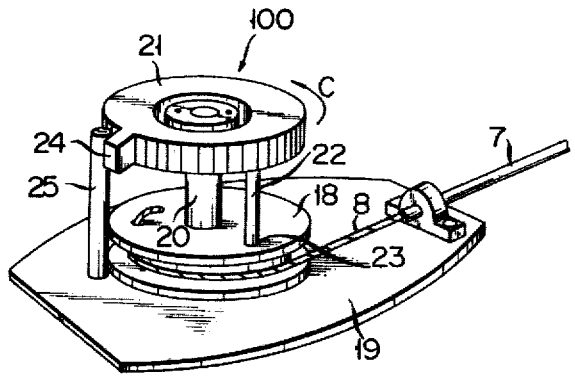
FIG. 5 is a perspective view of a takeup mechanism provided in the operation section of an endoscope shown in FIGS. 1 and 3.

Referring to FIG. 5, the takeup mechanism 100 comprises a takeup pulley 18 rotatably mounted on a shaft 20 fixed to the inner surface of a frame 19 of the operation section 1; and a return knob 21.

The proximal end of the operating wire section 8 is fixed to the takeup pulley 18. When the pulley 18 is rotated in a direction opposite to that of an arrow C shown in FIG. 5, the operating wire section 8 is taken up. The return knob 21 is provided, as shown in FIG. 1, on the outside of the operation section 1. One end of a connecting pin 22 is fixed to the lower surface of the return knob 21, and the other end of the pin 22 is inserted into an engaging hole 23 bored in the takeup pulley 18 in its axial direction. Turn of the return knob 21 causes the takeup pulley 18 to be rotated through substantially the same angle. The takeup pulley 18 can be rotated from the outside of the operation section 1 by means of the return knob 21. A projection 24 is formed on the periphery of the return knob 21 to protrude in its radial outward direction. Erected on the frame 19 is a stop pin 25. When the takeup pulley 18 is in a position just ready to commence the takeup of the operating wire section 8, the projection 24 abuts against that side of the upper end of the stop pin 25 which faces the backside of the drawing paper. As the operating wire 8 is taken up, the return knob 21 is rotated together with the pulley 18 in the direction opposite to that of an arrow C. When the return knob 21 is turned by substantially one rotation and the takeup of the operating wire section 8 by the takeup pulley 18 is completed, the projection 24 is pressed, as shown in FIG. 5, against that side of the upper end of the stop pin 25 which faces the front side of the drawing paper. On the other hand, as the return knob 21 begins to be rotated from the last mentioned condition in the direction of the arrow C (FIG. 5), the pulley 18 is also rotated in the same direction to gradually unwound the operating wire section 8, and then the projection 24 contacts the stop pin 25 after the return knob 21 makes substantially one rotation in the direction C, preventing the return knob 21 from making any further rotation, and the operating wire section 8 is unwound to the extent corresponding to the substantial one rotation of the return knob 21. Thus, the extended length of the wire section 8 toward the film chamber 5 is limited.

Figure 6:
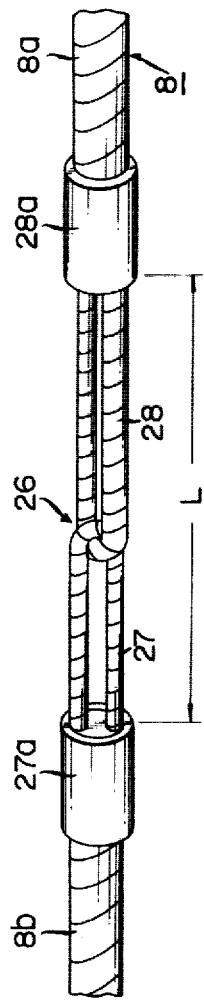
FIGS. 6 to 10 respectively show perspective views of embodiments of the wire length-adjusting means included in the film takeup device of this invention.
Figure 7:
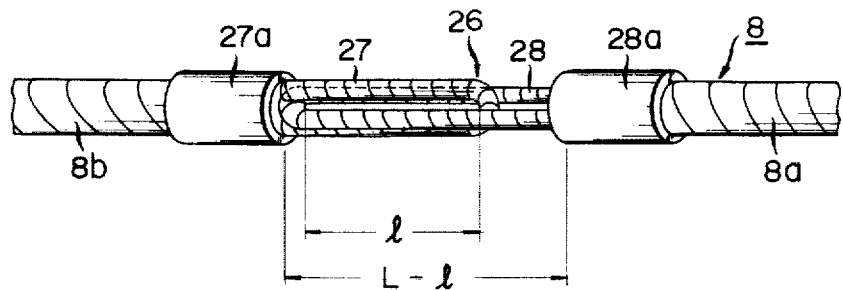

The operating wire section 8 comprises, as shown in FIGS. 3, 6 and 7, a metal operating wire 8a extending from the takeup pulley 18 to the proximity of the distal end 3 of the sheath 2; another metal operating wire 8b which is received in the distal end portion 3 of the sheath 2 and whose tip is fitted with the connector 9; and wire length-adjusting means or unit 26. This wire length-adjusting unit 26 is connected to the rear end of the operating wire 8b and the forward end of the operating wire 8a by the corresponding connectors 27a, 28a, thereby constituting two linked loops 27, 28 of metal wire.

Under the condition in which the operating wire section 8 is taken up on the takeup pulley 18, the mutually facing ends of the loops 27, 28 are linked together as shown in FIG. 6. Thus, the adjusting unit 26 is extended to the full to indicate a length L. Conversely, where the takeup pulley 18 is rotated by the return knob 21 in the unwinding direction D in FIG. 3 (in the direction of the arrow C shown in FIG. 5), the operating wire section 8a is moved to the left of FIG. 6. When the wire 8a is carried leftward, the linked end of the loop 28 is first eventually pressed, as shown in FIG. 7, against connector 27a and then the operating wire 8b together with the operating wire 8a travels leftward. As apparent from this operation, the wire length-adjusting unit 26 has its length contracted by the extent indicated by l in FIG. 7, namely, is defined to have a length expressed as L-l. In other words, the wire length-adjusting unit 26 provides a play of l. When the return knob 21 is fully rotated from the starting position to the terminal position, the operating wire 8a is carried forward by the takeup pulley 18 to such extent that the leading end of the operating wire 8b is extended into the film chamber 5, but does not touch the inner wall of the cap 6.

The respective frames of the film 11 are fed one after another when the takeup pulley 18 is rotated by a ratchet mechanism (not shown) each time to an extent corresponding to one tooth of a ratchet and the operating wire 8 is taken up to the corresponding extent. This film frame feeding operation is undertaken while the return knob 21 makes one rotation. While the operating wire 8 is unwound, the ratchet mechanism is disengaged from the takeup pulley 18 as in a conventional manner. The ratchet mechanism takes up the operating wire 8 with the reciprocation of a photographing lever 29 (FIG. 1) projecting out of the operation section 1 of the gastrocamera. After the return knob 21 is fully rotated in the unwinding direction until the projection 24 strikes the stop pin 25, the T-shaped engaging pin 10 provided at the leading end of the operating wire 8 is made to slightly project into the film chamber 5 as shown in FIG. 2. When the leading end of the operating wire 8b is pulled, the loops 27, 28 of the wire length-adjusting unit 26 have their relative position changed from that of FIG. 7 to that of FIG. 6. Therefore, the operating wire 8b can be more extended by the length l, as shown in FIG. 3. Accordingly, the connector 9 is fully taken out of the distal end portion 3 of the sheath 2, enabling the leading end 11a of the film 11 to be easily and reliably connected to the connector 9 and released therefrom.

Figure 8:
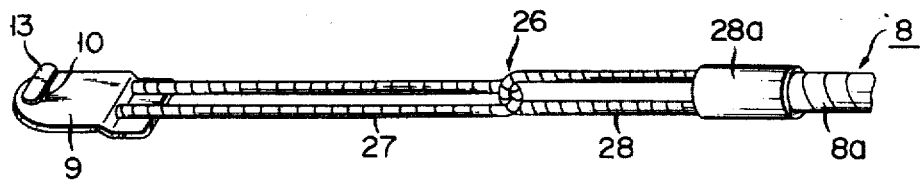

According to the embodiment of FIG. 8, a wire length-adjusting unit 26 is formed of two linked loops 27, 28 of wires, with the outer open end portions of one loop 27 directly fixed to the connector 9.

Figure 9:
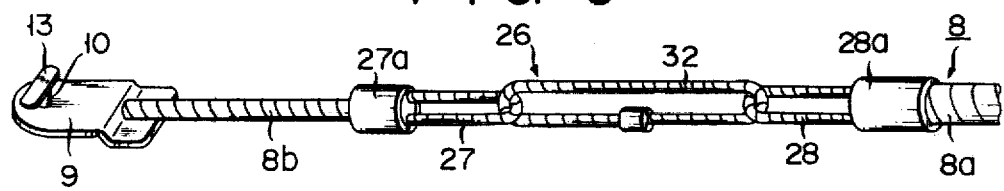

According to the embodiment of FIG. 9, a wire length-adjusting unit 26 is formed of three linked loops 27, 32, 28 of metal wires, thereby providing a larger play of the adjusting unit 26, namely, enabling the connector 9 to be drawn out of the distal end portion 3 of the sheath 2 for a greater distance.

Figure 10:
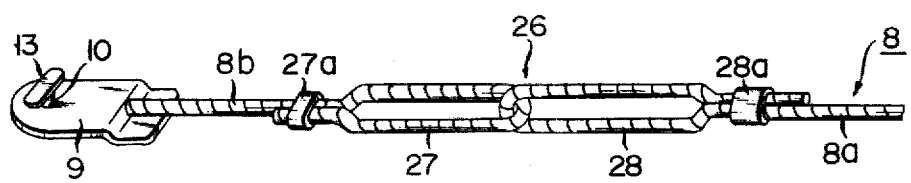

According to the embodiment of FIG. 10, a wire length-adjusting unit 26 is formed by folding the forward end portion of the operating wire 8a and the rear end portion of the operating wire 8b to respectively constitute two linked loops 28, 27, and fastening the open end portions of both loops 28, 27 by the corresponding connectors 28a, 27a. Unlike the embodiments of FIGS. 8 and 9, the wire length-adjusting unit 26 is formed of the operating wires themselves 8a, 8b, ensuring easy construction.

With the foregoing embodiments, a film cartridge was provided. However, any other type of film container may be used. FIG. 11 shows the case where a film cassette 35 is applied as a film container. The film cassette 35 is provided with a film takeup pulley 36, about which a film takeup wire 37 is wound. A looped connecting wire 39 whose outer closed end portion is twisted to form a very small loop 39a, and whose inner open end portions are connected to the connector 27a of the wire loop 27 of the wire length-adjusting unit 26. The leading end portion of the film takeup wire 37 is let to pass through the small loop 39a. The tip of the leading end portion of the film takeup wire 37 is fitted with a stop element 38, thereby preventing the film takeup wire 37 from coming off the small loop 39a.

With the embodiment of FIG. 12, the leading end portion of the film takeup wire 37 takes the form of a loop 40 to replace the stop element 38 of FIG. 11. Further, a connecting rod 42 is used in place of the connecting wire 39 of FIG. 11. An end of the connecting rod 42 is connected to the connector 27a of the loop 27 of the wire length-adjusting unit 26, and the other end of the connecting rod 42 is formed as a hook 41. The loop 40 is caught by the hook 41 to establish connection between the film takeup wire 37 and connecting rod 42.

The wire loops 27, 28 or 27, 28, 32 are disposed in the guide tube 7 and each has an elongated configuration as shown in FIGS. 3 and 6 to 12. As shown in FIGS. 3 and 11, each elongated wire loop has an outer crosswise width, i.e. the distance between the outer edges of the wire loop, smaller than the inner diameter of the guide tube 7 so that the loop can be easily reciprocated in the guide tube 7. Each elongated wire loop also has an inner crosswise width, i.e. the distance between the opposed inner edges of the wire loop, larger than the outer diameter of the wire constituting the wire loop linked to said wire loop. Thus, the adjacent loop can move relative to each other towards overlapping relationship and away from overlapping relationship in the guide tube without being obstructed by the adjacent loop or loops. During the operation of the wire length-adjusting unit 26, the closed wire loops are moved in the guide tube 7 and are not drawn out of the guide tube 7, whereby the closed wire loops do not tangle together outside of the guide tube 7 to be hindered from operating smoothly. Moreover, since the wire loops are elongated along and in the guide tube 7, the outer crosswise width of the loops is much smaller than the prior art round loops. Thus, the guide tube 7 is made small in its outer diameter so as to be installed in the sheath 2.

As mentioned above, the embodiments of FIGS. 1 to 12 enable the leading end portion 11a of the film 11 to be easily and reliably attached to the leading end portion of the film takeup wire 37 and detached therefrom. Therefore, the attachment and detachment can be undertaken easily and unmistakably even in a semi-dark chamber.

An endoscope provided with a film takeup device embodying this invention has the advantages that the distal end portion of an endoscope sheath need not be extended longer than the prior art type, enabling the endoscope to be easily inserted into the body cavity of a patient without causing him to feel great pain; and the wire length-adjusting unit is formed of linked loops of metal wires, assuring the easy manufacture of an inexpensive endoscope with a compact and light weight construction.

What is claimed is:

1. In an endoscope including an operation section, an elongated sheath having two ends, one end being connected to the operation section, a distal end portion connected to the other end of the sheath and provided with a camera and a rolled elongated piece of film therein having two ends, a guide tube extending lengthwise through the sheath and having an inner diameter, and a film takeup device, said film takeup device comprising a takeup mechanism provided at the operation section and an operating wire section extending lengthwise through the guide tube, said operating wire section having two end portions, one end portion being connected to the takeup mechanism and the other end portion being connected to one of the ends of the film for feeding the film frame by frame, each time the takeup mechanism is operated, said operating wire section including a series of elongated closed wire loops each constituted by a wire with an outer diameter, linked one after another and disposed in the guide tube for shortening the length of the operating wire section as the operating wire section is moved towards the distal end portion so as to move the adjacent loops towards overlapping relationship and for lengthening the operating wire section when the end portion of the operating wire section connected to the film is pulled out of the distal end portion so as to move the adjacent loops away from overlapping relationship, each of said closed wire loops having such an elongated configuration extending along the guide tube that each of said loops has a length longer than its width, an outer crosswise width along the entire length of each of said loops smaller than the inner diameter of the guide tube and an inner crosswise width along the entire length of each of said loops larger than the outer diameter of the wire of the closed wire loop linked to said each of the closed wire loops.

2. The film takeup device according to claim 1, wherein said one end portion of said operating wire section comprises an operating wire having two ends, one end being connected to the takeup mechanism and the other end being connected to one of the loops which is disposed nearest the operation section.

3. The film takeup device according to claim 2, wherein said one of said loops is integral with the operating wire.

4. The film takeup device according to claim 2, wherein said other end portion of said operating wire section comprises an operating wire having two ends, one end being connected to said one of said ends of the film and the other end being connected to one of said loops which is disposed remotest from the operation section.

5. In an endoscope including an operation section, an elongated sheath having two ends, one end being connected to the operation section, a distal end portion connected to the other end of the sheath and provided with a camera and a rolled elongated piece of film therein having two ends, a guide tube extending lengthwise through the sheath and having an inner diameter, and a film takeup device, said film takeup device comprising a takeup mechanism provided at the operation section and an operating wire section extending lengthwise through the guide tube, said operating wire section having two end portions, one end portion being connected to the takeup mechanism and the other end portion being connected to one of the ends of the film for feeding the film frame by frame, each time the takeup mechanism is operated, said operating wire section including a series of closed wire loops provided in a number of three each constituted by a wire with an outer diameter, linked one after another and disposed in the guide tube for shortening the length of the operating wire section as the operating wire section is moved towards the distal end portion so as to move the adjacent loops towards overlapping relationship and for lengthening the operating wire section when the end portion of the operating wire section connected to the film is pulled out of the distal end portion so as to move the adjacent loops away from overlapping relationship, each of said closed wire loops having such an elongated configuration extending along the guide tube that each of said loops has an outer crosswise width smaller than the inner diameter of the guide tube and an inner crosswise width larger than the outer diameter of the wire of the closed wire loop linked to said each of the closed wire loops.

* * * * *